US009763961B2

(12) United States Patent
Chen

(10) Patent No.: US 9,763,961 B2
(45) Date of Patent: Sep. 19, 2017

(54) COMPOSITIONS THAT MODULATE THE ACTIVITY OF ESTROGEN RECEPTORS AND ESTROGEN-RELATED RECEPTORS AND METHODS FOR USE

(75) Inventor: Shiuan Chen, Arcadia, CA (US)

(73) Assignee: CITY OF HOPE, Duarte, CA (US)

( * ) Notice: Subject to any disclaimer, the term of this patent is extended or adjusted under 35 U.S.C. 154(b) by 1372 days.

(21) Appl. No.: 11/400,024

(22) Filed: Apr. 6, 2006

(65) Prior Publication Data

US 2006/0241094 A1     Oct. 26, 2006

Related U.S. Application Data

(60) Provisional application No. 60/670,817, filed on Apr. 13, 2005.

(51) Int. Cl.
*A61K 31/56* (2006.01)

(52) U.S. Cl.
CPC .................................. *A61K 31/56* (2013.01)

(58) Field of Classification Search
CPC ...................................................... A61K 31/56
USPC ......................................................... 514/182
See application file for complete search history.

(56) References Cited

U.S. PATENT DOCUMENTS 3,817,308 A * 6/1974 Bundo ......................... 159/48.1
6,423,740 B1 * 7/2002 Bombardelli et al. ........ 514/445

FOREIGN PATENT DOCUMENTS

BE              892 662            9/1982

OTHER PUBLICATIONS

Dhar et al. "Chalcones. Condensation of Aromatic Aldehydes with Resacetophenone. II" Journal of Organic Chemistry, 1958, 23, 1159-1161.*
American Cancer Society's Cancer Facts and Figures, www.cancer.org (2003), 52 pages.
Ariazi, E. A., Clark, G. M. and Mertz, J. E. Estrogen-related receptor α and estrogen-related receptor γ associate with unfavorable and favorable biomarkers, respectively, in human breast cancer. *Cancer Research* 62:6510-6518 (2002).
Coward, P., Lee, D., Hull, M. V. and Lehmann, J. M. 4-Hydroxytamoxifen binds to and deactivates the estrogen-related receptor γ. *Proc. Natl. Acad. Sci.*, 98:8880-8884 (2001).
Detsi, A., Koufaki, M. and Calogeropoulou, T. Synthesis of (Z)-4-hydroxytamoxifen and (Z)-2-[4-[1-(p-hydroxyphenyl)-2-phenyl]-1-butenyl]phenoxyacetic acid. *J. Org. Chem.* 67:4608-4611 (2002).
Dodds, E. C., Golberg, L., Lawson, W. and Robinson, R. Synthetic oestrogenic compounds related to stilbene and diphenylethane I. *Proc. R. Soc. London Ser. B*. 127:140-167 (1939).
Gauthier, S., Mailhot, J. and Labrie, F. New highly stereoselective synthesis of (Z)-4-hydroxytamoxifen and (Z)-4-hydroxytoremifene via McMurry reaction. *J. Org. Chem.* 61:3890-3893 (1996).
Giguere, V. To ERR in the Estrogen Pathway. *Trends in Endocrinology & Metabolism, Review* 13(5):220-225 (2002).
Giguere, V., Yang, N., Segui, P. and Evans, R. M. Identification of a new class of steroid hormone receptors. *Nature* 331:91-94 (1988).
Ichida, M., Nemoto, S. and Finkel, T. Identification of a specific molecular repressor of the peroxisome proliferator-activated receptor γ Coactivator-1 γ (PGC-1γ). *J. Biol. Chem.* 52:50991-95 (2002).
Jarman, M. and McCague, R. The Use of Octafluorotoluene and Pentafluoropyridine in the Synthesis of Pure Z- and E-Isomers and Derivatives of Tamoxifen {1,2-Diphenyl-1-[4-(2-dimethylaminoethoxy)-phenyl]but-1-ene}. *J. Chem. Research (S)* 116-117 (1985).
Jordan, V. C. Antiestrogens and selective estrogen receptor modulators as multifunctional medicines. 1. Receptor interactions. *J. Medicinal Chem.* 46:883-908 (2003).
Karnik, P. S., Kulkarni, S., Liu, X. P., Budd, G. T. and Bukowski, R. M. Estrogen receptor mutations in tamoxifen-resistant breast cancer. *Cancer Research* 54:349-353 (1994).
Katzenellenbogen, B. S., Norman, M. J., Eckert, R. L., Peltz, S. W. and Mangel, W. F. Bioactivities, estrogen receptor interactions, and plasminogen activator-inducing activities of tamoxifen and hydroxyl-tamoxifen isomers in MCF-7 human breast cancer cells. *Cancer Research* 44:112-119 (1984).
Liu, D., Zhang, Z., Gladwell, W., and Teng, C, Estrogen Stimulates Estrogen-Related Receptor α Gene Expression Through Conserved Hormone Response Elements. *Endocrinology* 144(11):4894-4904 (2003).
Lubczyk, V., Bachmann, H. and Gust, R. Antiestrogenically active 1,1,2-tris(4-hydroxyphenyl)alkenes without basic side chain: synthesis and biological activity. *J. Med. Chem.* 46:1484-1491 (2003).
Lubczyk, V., Bachmann, H. and Gust, R. Investigations on estrogen receptor binding. The estrogenic, antiestrogenic, and cytotoxic properties of C2-alkyl-substituted 1,1-bis (4-hydroxyphenyl)-2-phenylethenes. *J. Med. Chem.*, 45:5358-5364 (2002).
Luo, J., Sladek, R., Carrier, J., Bader, J. A., Richard, D. and Giguere, V. Reduced fat mass in mice lacking orphan nuclear receptor estrogen-related receptor α. *Mol. Cell. Bio.*, 23:7947-7956 (2003).
McMurry, J.E. and Fleming, M.P. Improved procedures for the reductive coupling of carbonyls to olefins and for the reduction of diol to olefins. *J. Org. Chem.*, 41:896-897 (1976).
Mootha, V. K., Handschin, C., Arlow, D., Xie, X., St. Pierre, J., Sihag, S., Yang, W., Altshuler, D., Puigserver, P., Patterson, N., Willy, P. J., Schulman, I. G., Heyman, R. A., Lander, E. S. and Spiegelman, B. M. ERRα and Gabpa/b specify PGC-1α-dependent oxidative phosphorylation gene expression that is altered in diabetic muscle. *Proc. Natl. Acad. Sci.*, 101:6570-6575 (2004).
Riggs, L. and Hartman, L. Selective Estrogen-Receptor Modulators—Mechanisms of Action and Application to Clinical Practice. *New England Journal of Medicine* 348(7):618-629 (2003).
Riggs, L. and Hartman, L. Selective Estrogen-Receptor Modulators—Mechanisms of Action and Application to Clinical Practice. Corrections—*New England Journal of Medicine* 348(12):1192 (Mar. 20, 2003).

(Continued)

Primary Examiner — Yong Chong
(74) Attorney, Agent, or Firm — Perkins Coie LLP; Yingli Wang

(57) ABSTRACT

Disclosed are compositions for treating an estrogen receptor (ER) or estrogen related receptor (ERR) mediated disorder, comprising a therapeutically effective amount of a compound selected from the group consisting of Compound Nos. 1-9, 7-2, 7-4, 7-5, 7-7, 7-8, 8-2 and 3-15 set forth herein or a pharmaceutically acceptable salt thereof, wherein said compound modulates estrogen receptors and/or estrogen-related receptors and methods for use of said compositions.

27 Claims, 7 Drawing Sheets

(56) References Cited

OTHER PUBLICATIONS

Robertson, D. W., Katzenellenbogen, J.A., Long, D.J., Rorke, E.A. and Katzenellenbogen, B.S. Tamoxifen Antiestrogens. A Comparison of the Activity, Pharmacokinetics, and Metabolic Activation of the CIS and TRANS isomers of Tamoxifen. *J. Steroid Biochem.* 16:1-13 (1982).

Schneider, M. R. 2-Alkyl-substutited 1,1-bis (4-acetoxyphenyl)-2-phenylethenes. Estrogen receptor affinity, estrogenic and antiestrogenic properties, and mammary tumor inhibiting activity. *J. Med. Chem.* 29:1494-1498 (1986).

Schneider, M. R., von Angerer, E., Schonenberger, H., Michel, R. T. and Fortmeyer, H. P. 1,1,2-Triphenylbut-1-enes: relationship between structure, estradiol receptor affinity, and mammary tumor inhibiting properties. *J. Med. Chem.* 25:1070-1077 (1982).

Schreiber, S. N., Knutti, D., Brogli, K., Uhlmann, T., and Kralli, A. The Transcriptional Coactivator PGC-1 Regulates the Expression and Activity of the Orphan Nuclear Receptor Estrogen-Related Receptor α (ERRα). *J. Bio. Chem.* 278(11):9013-9018 (2003).

Schreiber, S. N., Emter, R., Hock, M. B., Knutti, D., Cardenas, J., Podvinec, M., Oakeley, E. J. and Kralli, A. The estrogen-related receptor α (ERRα) functions in PPARγ coactivator 1α (PGC-1α)-induced mitochondrial biogenesis. *Proc. Natl. Acad. Sci.*, 101:6472-6477 (2004).

Suetsugi, M., Su, L., Karlsberg, K., Yuan, Y.-C. and Chen, S. Flavone and isoflavone phytoestrogens are agonists of estrogen-related receptors. *Molecular Cancer Res.*, 1:981-991 (2003).

Sumi, D. and Ignarro, L. J. Estrogen-related receptor α1 up-regulates endothelial nitric oxide synthase expression. *Proc. Natl. Acad. Sci.*, 100:14451-14456 (2003).

Tremblay, G. B., Bergeron, D. and Giguere, V. 4-Hydroxytamoxifen is an Isoform-Specific Inhibitor of Orphan Estrogen-Receptor-Related (ERR) Nuclear Receptors β and γ. *Endocrinology* 142(10):4572-5 (2001).

Willy, P. J., Murray, I. R., Qian, J., Busch, B. B., Stevens, Jr., W. C., Martin, R., Mohan, R., Zhou, S., Ordentlich, P., Wei, P., Sapp, D. W., Horlick, R. A., Heyman, R. A. and Schulman, I. G. Regulation of PPARγ coactivator 1α (PGC-1α) signaling by an estrogen-related receptor α (ERRα) ligand. *Proc. Natl. Acad. Sci.*, 101:8912-8917 (2004).

Yang, C., Zhou, D., and Chen, S., Modulation of aromatase expression in the breast tissue by ERRα-1 orphan receptor. *Cancer Research* 58:5695-5700 (1998).

Zhou, D., Quach, K. M., Yang, C., Lee, S. Y., Pohajdak, B., and Chen, S. PNRC: a proline-rich nuclear receptor coregulatory protein that modulates transcriptional activation of multiple nuclear receptors including orphan receptors SF1 and ERRα1 (Estrogen Related Receptor α-1). *Molecular Endocrinology* 14:986-998 (2000).

\* cited by examiner

COMPOSITIONS THAT MODULATE THE ACTIVITY OF ESTROGEN RECEPTORS AND ESTROGEN-RELATED RECEPTORS AND METHODS FOR USE

CROSS-REFERENCE TO RELATED APPLICATION

The present application claims priority to U.S. Provisional Application No. 60/670,817 (Chen), filed Apr. 13, 2005, the disclosure of which is incorporated by reference herein in its entirety, including drawings.

STATEMENT OF GOVERNMENT INTEREST

This invention was supported in part by NIH Grant No. ES08258. The United States government may have certain rights in this invention.

FIELD OF THE INVENTION

This invention relates to compounds that modulate the activity of estrogen receptors (ERα,β or ERa,b) and estrogen-related receptors (ERRα,β,γ or ERRa,b,g) and methods for use of said compounds.

BACKGROUND OF THE INVENTION

Each of the references cited herein is incorporated by reference in its entirety. A complete listing of the citations is set forth at the end of the specification.

An estimated 211,300 new cases of invasive breast cancer are expected to occur among women in the United States during 2003. Breast cancer is the most frequently diagnosed non-skin cancer in women. (1) Estrogen is a steroid hormone that, while having important functions including the control of reproduction and the development of secondary sexual characteristics, also plays a predominant role in breast cancer growth and development. The use of estrogen for its positive effects can also detrimentally result in the stimulation of other tissues, such as those of the breast and uterus, and increase the risk of cancer at these sites.

The estrogen receptor (ER) is a member of a nuclear receptor superfamily consisting of orphan receptors and receptors for classic high-affinity ligands, such as steroid hormones, vitamin D, retinoids, and thyroid hormones. As a ligand inducible transcription factor, the estrogen receptor mediates the activity of estrogen in the development and function of the female reproductive system, the maintenance of bone mineral density, regulation of blood lipid profile, brain function, cardiovascular health and other physiologic processes.

Estrogen-Related Receptors (ERRs) are included in the nuclear receptor family and were the first orphan nuclear receptors found through a search for genes encoding proteins related to known nuclear receptors. While it was originally believed that the development and physiological roles of ERRs were quite distant from those of the classic ERs, it has recently been shown that in some cases ERRs can share target genes, coregulatory proteins, ligands, and sites of action with the ERs. (2) Like ER, ERRs are also implicated in breast cancer and other diseases. (3)

(Z)-Tamoxifen (Z-TAM), (Z)-2-[4-(1,2-diphenyl-1-butenyl) phenoxy]N,N-dimethylethanamine, is used clinically to treat estrogen-dependent breast cancer by acting as an antagonist of estrogen-induced tumor growth. The mechanism for its principal action is its competition with the natural agonist hormone estradiol ($E_2$) for binding to the estrogen receptor ligand-binding domain, thereby reducing the ability of estradiol to stimulate nuclear transcription and consequent cell growth. For example, it is known that (Z)-4-hydroxytamoxifen (4-OHT), a potent tamoxifen metabolite, is a selective estrogen-receptor modulator that functions as an antagonist in breast cancer cells but displays estrogen-like activities in the uterus and bone. The Z-4-OHT form isomer has the required antiestrogenic activity, but E-4-OHT isomer has only about 5% of its affinity for ER. (17)

Selective Estrogen-Receptor Modulators (SERMs) are a type of estrogen receptor ligand that can exert agonist, antagonist, or neutral effects, depending on factors including the target gene and/or target tissue. (2) SERMs properties are related to their ability to compete in target tissues with estradiol for binding sites in the ligand-binding domain (LBD) of the ER. Tamoxifen and particularly its metabolite 4-hydroxytamoxifen are SERMs that also antagonize ERRs, but much higher doses of those SERMs are required to antagonize ERRs than ERs. In recent studies examining whether other ER ligands could influence ERR activity, (Z)-4-OHT was identified as the most potent isoform-specific inhibitor of ERRβ,γ. (4) The structures of (Z)-TAM, (Z)-4-OHT, and $E_2$ are:

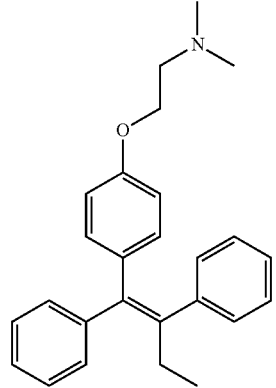

Z-TAM

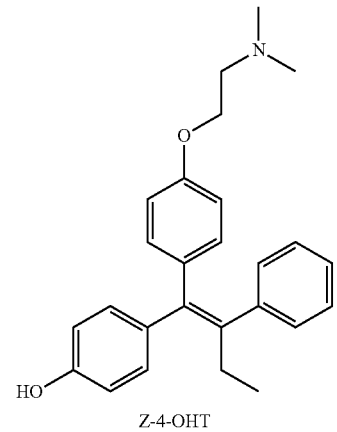

Z-4-OHT

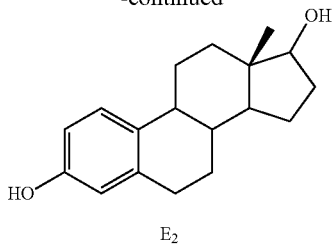

E₂

Recent experiments have synthesized 1,1-bis and 1,1,2-tris (4-hydroxyphenyl)-2-phenylalkene analogs for the studies of their antagonist action. (5) Studies also have shown that 1,1,2-triarylethenes are antagonists and that they inhibit the effect of 1 nN E$_2$, dependent on the length of C2-alkyl chain. When C2 is substituted by an ethyl or trifluoromethyl group of the 1,1,2-triarylethene system, the substituted compound possesses the same antagonistic potency as 4-hydroxytamoxifen and is almost 50 times more active than tamoxifen itself. (6)

None of the 1,1-bis- and 1,1,2-tri (4-hydroxyphenyl)-2-phenylalkylenes bear a basic side chain, which is responsible for antagonistic effects of ER. Removal of the dimethylaminoethoxy side chain of 4-hydroxytamoxifen did not decrease the antagonistic effects on the MCF-7-2a cell line. This finding indicated that, in the class of 1,1-bis- and 1,1,2-tris (4-hydroxyphenyl)-2-phenylalkenes, having a basic side chain is not a prerequisite for exhibiting high binding affinity and antagonistic effects on ER. The antiestrogenic properties comprising estrogen receptor binding depend only on the length of the C2-alkyl chain.

Other experiments have also revealed information about the various ERRs. Estrogen Related Receptor Alpha (ERRα or ERRa or ERRa-1 or ERRα-1) binds the ligand diethylstilbestrol (DES) with greater affinity than 4-hydroxytamoxifen as antagonist/inverse agonist. ERRα functions to control adiposity and energy metabolism. In experiments with ERRα knockout mice, the mice are lean. ERRα also regulates the medium-chain acyl-CoA dehydrogenase (MCAD) gene in conjunction with PGC-1α (peroxisome proliferator-activated receptor gamma coactivator 1), a key regulator of lipid and glucose homeostasis.

PGC-1α is a transcriptional co-activator that regulates numerous pathways controlling both metabolism and overall energy homeostasis. (15) ERRα binding to PGC-1α requires the AF2 domain of ERRα. PGC-1α induces the expression of ERRα, meaning that ERRα is upregulated in response to signals that induce PGC-1α, such as exposure to cold. Expression of PGC-1α led to the induction of ERRα at the RNA and protein level in SAOS2-GR(+) cells, as well as in HtTA-1, HepG2, and 293 cells.

It has been found that PGC-1α and ERRα have a similar pattern of expression in human tissues, with both being present predominantly in organs with high metabolic needs such as skeletal muscle, kidney, and heart. Physiological stimuli such as fasting coordinately induces PGC-1α and ERRα. ERRα can dramatically and specifically repress PGC-1α transcriptional activity. (7)

ERRα is known to be expressed in breast cancer cells and it inhibits breast cancer cell growth independent of the estrogen receptor. ERRα regulates aromatase and pS2 genes and is associated with unfavorable biomarkers in human breast cancer. ERRα is also expressed in osteoblasts and regulates osteopontin expression. A recent study demonstrates that the ERRα gene is a downstream target of ERα. (16)

Further, ERRα has been shown to modulate oxidative phosphorylation gene expression that is altered in diabetic muscle. (25-27) It was suggested that ERRα agonists might ameliorate insulin-resistance in individuals with type 2 diabetes mellitus, and therefore that its antagonists could play roles in the development of diabetes.

Estrogen Related Receptor Beta (ERRβ or ERRb) binds the ligand 4-hydroxytamoxifen with a greater affinity than DES as antagonist/inverse agonist. ERRβ controls trophoblast proliferation and placental function. In mice lacking ERRβ, trophoblast stem cell differentiation is impaired and the placenta fails to develop normally. (8) ERRβ is present early in the developing placenta in a subset of cells in extra-embryonic ectoderm destined to make up the chorion. (8,9) Thus, ERRβ is likely essential for reproduction. ERRβ synthesis is highly restricted in postnatal life, being detected at low levels in the liver, stomach, skeletal muscle, heart and kidney. (5)

Estrogen Related Receptor Gamma (ERRγ or ERRg) binds the ligand 4-hydroxytamoxifen with a greater affinity than DES as antagonist/inverse agonist. ERRγ is expressed in heart, skeletal muscle, kidney, and brain as well as in the developing nervous system. Human ERRγ transcripts can be detected at very high levels in fetal brain, and at lower levels in fetal kidney, lung and liver. (4) In adult tissues, ERRγ is widely expressed and can be detected in brain, lung, bone marrow, adrenal and thyroid glands, trachea and spinal cord. In the mouse, the gene encoding ERRγ is expressed in specific areas of the brain, in addition to the heart, kidney, muscle, spleen and testis. With respect to its role in breast cancer, ERRγ associates with favorable biomarkers in human breast cancer and may regulate MCAD.

ERRα, ERRβ, and ERRγ do not respond to natural estrogens. They do recognize, however, the estrogen response element and can modulate gene expression in the absence of exogenously added ligand. 4-OHT disrupts the interaction between ERRβ and its co-regulator proteins and ERRγ and its co-regulator proteins. 4-OHT also abolishes the constitutive transcriptional activity of these receptors in transient transfection assays. In contrast, 4-OHT has no effect on coregulator/ERRα interaction or its transcriptional activity, demonstrating the existence of a novel nuclear receptor-based pharmacological pathway that may contribute to the tissue-specific activities of 4-OHT. (10)

In addition, we have found that found that ERRs can up-regulate aromatase expression in breast cancer cells. Therefore, antagonists of ERRs can be useful to treat breast cancer by the suppression of ERR activity and the reduction of estrogen formation. (21)

Thus, ERs and ERRs are targets of modulation. There is a pressing need, however, for compounds that modulate these receptors more effectively. There is also a need for methods of using these compounds to treat estrogen-related disorders.

SUMMARY OF THE INVENTION

One embodiment of the present invention is a composition for treating an estrogen receptor (ER) or estrogen related receptor (ERR) mediated disorder, comprising a therapeutically effective amount of a compound selected from the group consisting of Compound Nos. 1-9, 7-2, 7-4, 7-5, 7-7, 7-8, 8-2, and 3-15 set forth herein or a pharmaceutically acceptable salt thereof, wherein said compound modulates estrogen receptors and/or estrogen-related receptors. Modulation of the ERs and ERRs occurs through the action the composition antagonizing or agonizing the receptors. The composition may modulate both ERs and ERRs simultaneously.

Another embodiment of the present invention is a method for modulating the biological activity of an estrogen receptor and or estrogen related receptor, comprising exposing said estrogen receptor and/or estrogen related receptor to a compound selected from the group consisting of Compound Nos. 1-9, 7-2, 7-4, 7-5, 7-7, 7-8, 8-2, and 3-15 or pharmaceutically acceptable salt thereof.

Another embodiment of the present invention a method for the treatment of diseases or disorders relating to the ERs and/or ERRs. The disease may be proliferative diseases, obesity, stroke, hormonal disorders, lipidemia and other lipid disorders, metabolic disorders, Syndrome X, diabetes, diseases related to fetal development, osteoporosis or heart disease. The method comprises administering at least one of Compound Nos. 1-9, 7-2, 7-4, 7-5, 7-7, 7-8, 8-2, and 3-15 to a subject in need thereof in a pharmaceutically acceptable carrier and in a pharmaceutically effective amount. Preferably, the administration is repeated to maintain a therapeutically effective amount in the blood stream and/or at the location of the disease or disorder over time until treatment is effected.

In another embodiment, the administration of at least one of Compound Nos. 1-9, 7-2, 7-4, 7-5, 7-7, 7-8, 8-2, and 3-15 is preferably by the oral, intravenous, parenteral, nasal, or transdermal route. The combined dosage of the at least one novel compound may be between 1 mg/day and 1 g/day, between 20 mg/kg and 750 mg/kg per day, or between 50mg/day and 500 mg/day.

These and other aspects of the present invention are elucidated further in the detailed description.

DETAILED DESCRIPTION

Definitions

Figure 1:
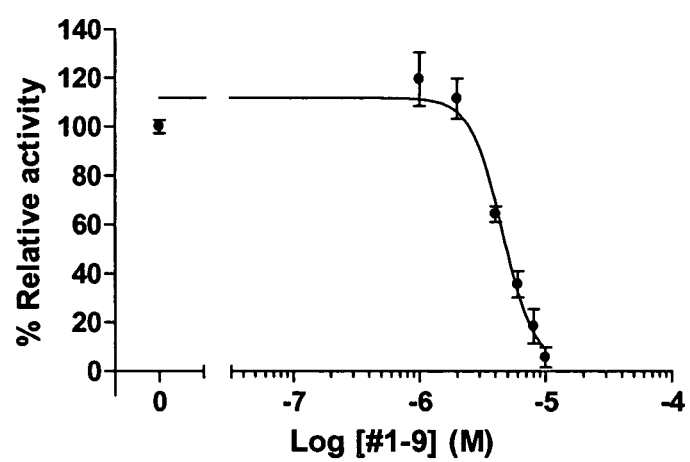
FIG. 1 shows the antagonist activity of Compound No. 1-9 (2',4'-Dihydroxy-2,3-dimethoxychalcone) in transient transfection with full length human ERRα-1 and SF1 binding site containing luciferase reporter.

The present invention can best be understood in light of the following definitions.

Generally, an "antagonist" is a ligand that interacts with or binds to its receptor or ligand binding domain to down-regulate, suppress, or inhibit an activity mediated by said receptor or ligand binding domain. For example, an ER or ERR antagonist means a molecule or a compound that inhibits or decreases the transcriptional activity of ER or ERR, respectively.

The term "agonist" as used herein refers to a ligand that interacts with or binds to its receptor or ligand binding domain to upregulate, increase, or induce an activity mediated by said receptor or ligand binding domain. For example, an ER or ERR agonist means a molecule or a compound that induces or increases the transcriptional activity of ER or ERR, respectively.

The term "pharmaceutically effective dose" as used herein refers to the amount of either a novel compound or novel compound composition comprising one or more of the novel compounds described herein that produces a desired therapeutic effect, such as treating the target disease. The precise amount of the pharmaceutically effective dose of a novel compound or novel compound composition that will yield the most effective results in terms of efficacy of treatment in a given subject will depend upon the activity, pharmacokinetics, pharmacodynamics, and bioavailability of a particular ERR agonist or antagonist, physiological condition of the subject (including age, sex, disease type and stage, general physical condition, responsiveness to a given dosage and type of medication), the nature of pharmaceutically acceptable carrier in a formulation, and a route of administration, among other potential factors. Those skilled in the clinical and pharmacological arts will be able to determine these factors through routine experimentation consisting of monitoring the subject and adjusting the dosage. Remington: The Science and Practice of Pharmacy (Gennaro ed. 20$^{th}$ edition, Williams & Wilkins Pa., USA) (2000).

As used herein, the "target disease" may be any disease in which modulating one or more of the ERs, ERRs or a combination of modulating both ERs and ERRs treats the disease. Without limitation, a list of target diseases includes cancer and other proliferative disease, obesity, stroke, hormonal disorders, lipidemia and other lipid disorders, metabolic disorders, Syndrome X, diabetes, diseases related to fetal development, osteoporosis or heart disease. While it is possible for a novel compound to be administered as a pure or substantially pure compound, it is preferable that the ER or ERR be administered as a composition in the form of pharmaceutical formulations or preparations suitable for a particular administration route. A novel compound composition comprises one or more ER and/or ERR modulators and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting one or more ER or ERR modulators from one tissue, organ, or portion of the body, to another tissue, organ, or portion of the body. Each component must be "pharmaceutically acceptable" in the sense of being compatible with the other ingredients of the formulation. It must also be suitable for use in contact with the tissue or organ of humans and animals without excessive toxicity, irritation, allergic response, immunogenecity, or other problems or complications, commensurate with a reasonable benefit/risk ratio. The novel compounds may also be encapsulated with liposomes.

A "route of administration" for a novel compound or composition can be by any pathway known in the art, including without limitation, oral, enteral, nasal, topical, rectal, vaginal, aerosol, transmucosal, transdermal, ophthalmic, pulmonary, and/or parenteral administration. A parenteral administration refers to an administration route that typically relates to injection. Parenteral administration includes, but is not limited to, intravenous, intramuscular, intraarterial, intraathecal, intracapsular, infraorbital, intracardiac, intradermal, intraperitoneal, transtracheal, subcutaneous, subcuticular, intraarticular, subcapsular, subarachnoid, intraspinal, via intrasternal injection, and/or via infusion.

"Treatment" of or "treating" a disease may mean preventing the disease by causing clinical symptoms not to develop, inhibiting the disease by stopping or reducing the symptoms, the development of the disease, and/or slowing the rate of development of the disease, relieving the disease by causing a complete or partial regression of the disease, reducing the risk of developing the disease, or a combination thereof.

The term "contacted" when applied to a cell, tissue or organ means the process by which a novel compound or compound composition is delivered to the target cell, tissue or organ, or placed in direct proximity of the cell, tissue, or organ.

"Therapeutically effective amount" is the amount of novel compound or composition that, when administered to a subject, is effective to bring about a desired effect. In this case, that effect is typically an antagonistic effect that ultimately decreases the activity of the ERs and/or ERRs. The preferred therapeutically effective amount is in an amount of between 1 mg/day and 1 g/day, more preferably between 20 mg/kg and 750 mg/kg per day, and most preferably between 50mg/day and 500 mg/day.

"Radiotherapeutic agents" or "chemotherapeutic agents" mean any chemical compound or treatment method that induces cell damage and/or results in cell death. Such agents include azathioprine, BCG, androgens, asparagine, bleomycin, epirubicin, gemcitabine, hydroxyurea, interferon alpha, beta or gamma, 6-mercaptopurine, paclitaxel, thioguanine, adriamycin, 5-fluorouracil, etopside, camptothecin, actinomycin-D, mitomycin C, cisplatin, or other drugs. The agents may also include radiation and waves like gamma radiation, X-rays, UV-irradiation, microwaves, and electroemissions. Other chemotherapeutic substances may include natural or synthetic antibodies, metastases-inhibiting compounds, growth factor inhibitors, oncogenic protein inhibitors, such as for inhibiting RAS, protein kinase inhibitors, or DNA topoisomerase inhibitors. These agents may be used in conjunction with the compounds disclosed herein as an initial treatment or as part of a second-line therapy for tamoxifen-resistant breast cancer. The invention contemplates the use of any of these, alone or in combination, with the compounds disclosed herein and methods of their use.

"Pro-drug" means any compound that releases a biologically active compound of one or more of the compounds disclosed herein in vivo when administered to a subject because there are in vivo modifications of the functional groups that yield the desired compound.

Agonists and Antagonists of ERRs

The following compounds (or pharmaceutically acceptable salt or pro-drug thereof) have been identified has antagonists of ERs and/or ERRs:

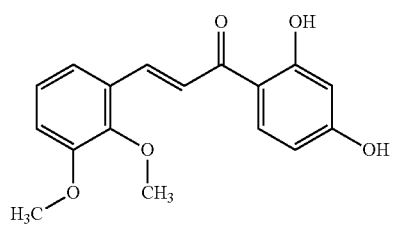

Compound 1-9

2',4'-Dihydroxy-2,3-dimethoxychalcone

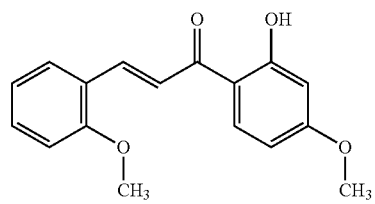

Compound 7-2

2,4'-Dimethoxy-2'-hydroxychalcone

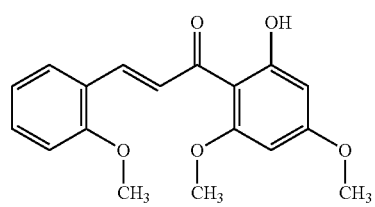

Compound 7-4

2'-Hydroxy-2,3,4',-trimethoxychalcone

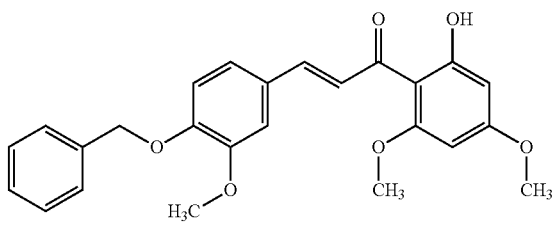

Compound 7-5

2,2',4'-Trihydroxychalcone

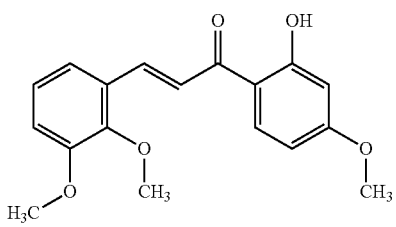

Compound 7-7

2'-Hydroxy-2,4,4'-trimethoxychalcone

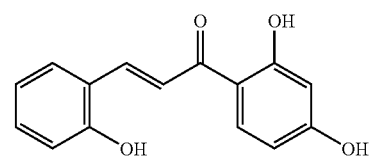

Compound 7-8

2,2',4'-Trihydroxychalcone

-continued

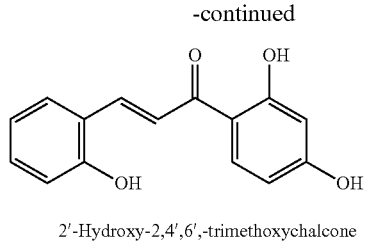

Compound 7-8

2'-Hydroxy-2,4',6',-trimethoxychalcone

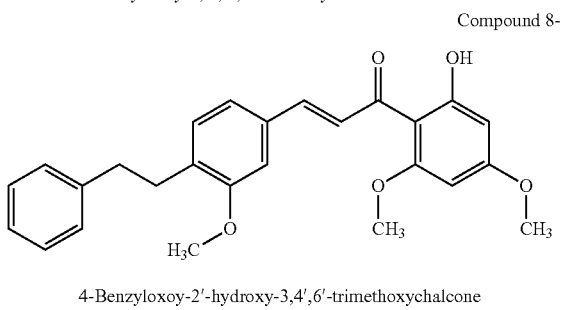

Compound 8-2

4-Benzyloxoy-2'-hydroxy-3,4',6'-trimethoxychalcone

The following compound (or pharmaceutically acceptable salt or pro-drug thereof) has been identified as agonists of ERs and/or ERRs.

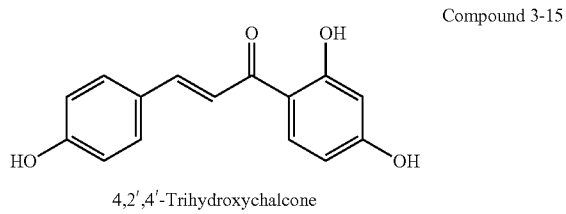 [SMILES: O=C(/C=C/c1ccc(O)cc1)c1ccc(O)cc1O]

Compound 3-15

4,2',4'-Trihydroxychalcone

In addition to the compounds set forth herein, pharmaceutically acceptable derivatives of the compounds are provided herein. Such derivatives include salts, esters, acids, bases, solvates, hydrates and prodrugs.

Experimental Procedures

Several ERR ligand functional assays have been performed to confirm the ligand interaction with ERRs.

Procedure 1—Mammalian Cell Transfection and Luciferase Assays

HeLa cells were cultured in MEM Earle's salts medium supplemented with 5% charcoal/dextran-treated fetal bovine serum. Cells were then divided and cultured in 6-well plates until 80% confluence was achieved. The cells were next transfected with 4 μg Lipofectin. An equal amount of total DNA was used in all transfections by including appropriate amounts of the empty vector, pSG5, in addition to specific amounts of pSG5-ERRα and luciferase reporter plasmids (ERRE (ERRα recognizes an ERE half site)-containing reporter and aromatase promoter I.3-containing reporter). Following an overnight incubation, the medium containing Lipofectin and DNA was removed, and the cells cultured in a growth medium containing 5% charcoal/dextran-treated fetal bovine serum with or without ligands. After a 24-hour incubation, the cells was harvested from the plates by scraping, and the luciferase activities in the cell lysates (with the same amounts of protein) was measured according to the manufacturer's instructions (Promega). All experiments were performed in triplicate.

Figure 2:
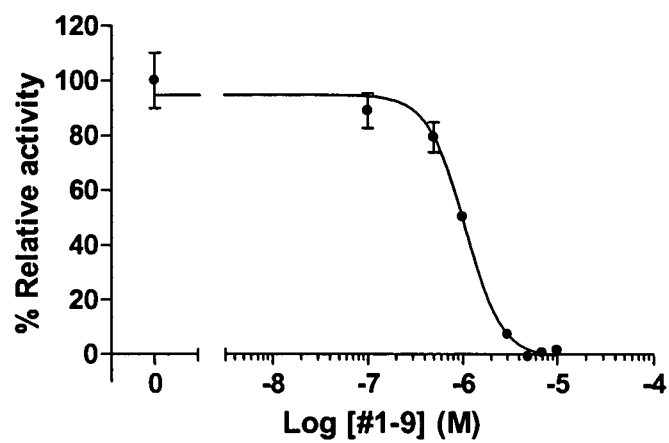
FIG. 2 shows antagonist activity of Compound No. 1-9 (2',4'-Dihydroxy-2,3-dimethoxychalcone) in transient transfection with GAL4-human ERRα-1 LBD fusion and GAL4 binding site containing luciferase reporter.

Referring to FIG. 2, we have also prepared GAL4-ERRα expression plasmid and luciferase reporter plasmids with GAL4 response element. This is a more sensitive assay method than that using pSG5-ERRα and ERE luciferase reporter plasmids.

Procedure 2—Mammalian Two-Hybrid Assays

HeLa cells were transiently transfected with 0.5 μg reporter plasmid, Gal4-luciferase (Clontech), and 0.5 μg PM-ERRα LBD, along with 0.5 μg pVP-PNRC270-327. PNRC is a nuclear receptor coactivator protein identified in our laboratory. (29) These plasmid constructs have been generated and are described in detail in the paper published by Suetsugi, et al. (28)

Procedure 3—Ligand Binding Affinity Analysis

In order to directly measure the binding affinities of agonists and inverse agonists to ERRα, we performed a competitive ERR binding whole cell assay using ERRα-positive SK-BR-3 cells. This method is developed based on the ER binding assay posted by the National Toxicology Program at the NIEHS <<http://iccvam.niehs.nih.gov/methods/endodocs/final/erbndbrd/erbdappx/B1.pdf>>. Briefly, the cultured SK-BR-3cells were incubated for 1 hour with 1 μM [3H] genistein (American Radiolabeled Chemicals, Inc., St. Louis, Mo.) or investigated compound (X) at concentrations from 1 nM to 1 μM. We have shown that genistein is an agonist of ERRα. After the cells were washed twice with PBS, 250 μl ethanol will be added to each well for 20 min. Aliquots of ethanol extract was mixed with scintillation liquid for radioactivity measurements. The experiments have been performed in triplicate. The relative binding affinity was estimated as [(IC50)genistein/(IC50)X]×100.

Figure 8:
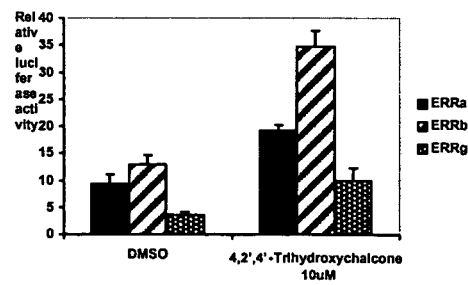
FIG. 8 shows the relative luciferase activity of Compound No. 3-15 (4,2',4'-trihydroxychalcone) and DMSO for ERRα/β/γ.

Referring to Tables 1 and 2 and FIG. 8, Compound Nos. 1-9, 7-2, 7-4, 7-5, 7-7, 7-8, 8-2, and 3-15 are shown to agonize or antagonize ERs and ERRs with varying degrees of success. Many of the data show that the Compound Nos. 1-9, 7-2, 7-4, 7-5, 7-7, 7-8, 8-2, and 3-15 are more efficacious than compounds presently known in the art at modulating ERs, ERRs or modulating both ERs and ERRs.

Figure 7:
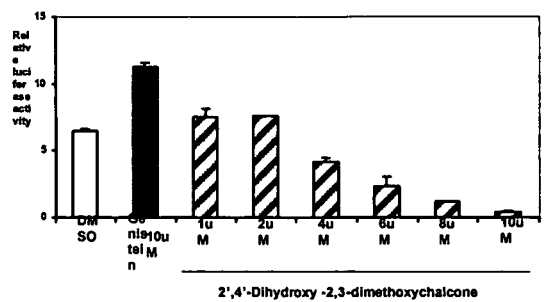
FIG. 7 shows the relative luciferase activity of Compound No. 1-9 (2',4'-Dihydroxy-2,3-dimethoxychalcone) at various concentrations, Genistein and dimethyl sulfoxide (DMSO), for ERRα.

FIG. 7 shows that Compound No. 1-9 (2',4'-Dihydroxy-2,3-dimethoxychalcone) can suppress the constitutive activity of ERRα (compared to the dimethyl sulfoxide (DMSO) control) in a dose-dependent manner. The 2-methoxyl group may be important for the antagonistic activity of the chalcone. Through transient transfection assays, the IC50 values for Compound No. 1-9 are between 0.7 to 2 μM. We believe that these chalcones are good lead compounds to further develop ERR ligands with high affinity. At the present time, only one additional group has reported the identification of an inverse agonist of ERRα, i.e., XCT790 that has an IC50 value of 0.4 μM. (27)

Referring to FIG. 8, Compound No. 3-15 (4,2',4'-trihydroxychalcone), has been found to be an agonist of all three forms of ERRs.

Since Compound Nos. 1-9, 7-2, 7-4, 7-5, 7-7, 7-8, and 8-2 are antagonists of ERs and/or ERRs, an embodiment of the present invention provides a method for treating any disease or disorder that is caused or worsened by the presence of estrogen, estrogen receptors, and/or estrogen related receptors, and/or estrogen, estrogen receptor and/or estrogen related receptor mediated activity. This embodiment also encompasses any disease that can be treated with an ERR antagonist, such as cancer, including breast cancer, or any other disease set forth herein. The disease can be treated by administering a composition of a pharmaceutically effective dose of one or more of the Compound Nos. 1-9, 7-2, 7-4, 7-5, 7-7, 7-8, and 8-2 to the subject in need of treatment. These compounds are estrogen receptor and estrogen related receptor antagonists. In one embodiment, the subject is human.

Another aspect of the present invention provides a method for increasing the efficacy of a variety of treatments for diseases, such as breast cancer and other disease set forth herein, by using the antagonizing Compound Nos. 1-9, 7-2, 7-4, 7-5, 7-7, 7-8, and 8-2 in conjunction with other methods of cancer treatment such as radiotherapeutic agents or chemotherapeutic agents.

Since the Compound No. 3-15 is an agonist, which enhances, induces or promotes the activity of ERs and ERRs as set forth herein, an aspect of the present invention provides a method for treating any disease that is caused or worsened by the absence of estrogen, estrogen receptors, and/or estrogen related receptors, and/or estrogen, estrogen receptor and/or estrogen related receptor mediated activity. This embodiment also encompasses any disease that can be treated with an ER or ERR agonist, including any disease set forth herein. The disease can be treated by administering a composition of a pharmaceutically effective dose of the Compound No. 3-15 to the subject in need of treatment. In one embodiment, the subject is human.

Another aspect of the present invention provides a method for increasing the efficacy of a variety of treatments for diseases, such as breast cancer and other disease set forth herein, by using the agonizing Compound No. 3-15 in conjunction with other methods of cancer treatment such as radiotherapeutic agents or chemotherapeutic agents.

EXAMPLES

Example 1

Demonstration of the Antagonistic Properties of Chalcones by Mammalian Cell Transfection Experiments in HeLa Cells To evaluate the functional significance of the interaction of chalcones with ERRα, we incubated these compounds with HeLa cells which were transiently transfected with human ERRα expression plasmid and a luciferase reporter plasmid containing SF1 binding site. Through these experiments, we identified the chalcones of Compound Nos. 1-9, 7-2, 7-4, 7-5, 7-7, 7-8, and 8-2 as antagonists of ERRα. These chalcones suppressed the constitutive activity of ERRα in a dose-dependent manner as shown in FIG. 1, and their IC50 values were mostly between 5 and 10 mM as shown in Table 1. In order to confirm the results above, HeLa cells were transiently transfected with GAL4-human ERRα LBD fusion expression plasmid and a luciferase reporter plasmid containing GAL4 binding site. As shown in FIG. 2, those chalcones suppressed the constitutive activity of ERRα in a dose-dependent manner, and their IC50 values were between 900 pM and 5 mM per FIG. 1. These results indicate that Compound No. 1-9 is the most potent antagonist among these chalcones. Most of the compounds, however, have similar IC50 value, and have a similar potency.

TABLE 1

| IC50 Value of Chalcones in transient transfection assay with ERRα-1 | | |
|---|---|---|
| | IC50 (μM)*** | |
| Compound No. | SF1-SV40-Luc* | Gal4-TK-Luc** |
| 1-9 | 5.7 ± 1.8 | 1.1 ± 0.7 |
| 7-2 | 8.3 ± 0.4 | 2.0 ± 0.7 |
| 7-4 | 7.7 ± 0.8 | 2.0 ± 1.0 |

TABLE 1-continued

| IC50 Value of Chalcones in transient transfection assay with ERRα-1 | | |
|---|---|---|
| | IC50 (μM)*** | |
| Compound No. | SF1-SV40-Luc* | Gal4-TK-Luc** |
| 7-5 | 6.2 ± 1.0 | 0.9 ± 0.4 |
| 7-7 | 18.7 ± 7.4 | 3.6 ± 1.1 |
| 7-8 | 6.4 ± 1.0 | 1.9 ± 0.8 |
| 8-2 | 8.7 ± 0.3 | 2.4 ± 1.7 |

*HeLa cells were cotransfected with pSG5-ERRα (0.5 mg) and luciferase reporter plasmid containing SF1 binding site and SV40 promoter (0.25 mg).
**HeLa cells were cotransfected with pM-ERRα LBD (0.5 mg) and luciferase reporter plasmid containing GAL4 binding site and TK promoter (0.25 mg).
*, **The transfected cells were incubated with Compound No. 1-9 for 24 h. After cells were washed with 1× PBS, luciferase activity was measured.
***Values represent the mean ± SD.

Referring to FIG. 1, HeLa cells were cotransfected with pSG5-ERRα (0.5 μg) and luciferase reporter plasmid containing SF1 binding site and SV40 promoter (0.25 μg). The transfected cells were incubated with Compound No. 1-9 for 24 h. After cells were washed with 1× PBS, luciferase activity was measured. Values represent the mean±SD.

Referring to FIG. 2, HeLa cells were cotransfected with pM-ERRα LBD (0.5 μg) and luciferase reporter plasmid containing GAL4 binding site and TK promoter (0.25 μg). The transfected cells were incubated with Compound No. 1-9 for 24 h. After cells were washed with 1× PBS, luciferase activity was measured. Values represent the mean±SD.

In addition to ERRα, interaction of the chalcones of Compound Nos. 1-9, 7-2, 7-4, 7-5, 7-7, 7-8, and 8-2 with other isoforms of ERR (ERRb, ERRg), ERa and ERb were investigated by transient transfection experiments. As shown in Table 2, Compound Nos. 1-9, 7-2, 7-4, 7-5, 7-7, 7-8, and 8-2 showed antagonistic properties on ERRb, ERRg, ERa and ERb in a dose-dependent manner. These findings indicate that these seven chalcones are antagonists of the isoforms of ER and ERR.

TABLE 2

| IC50 values off chalcones in transient transfection assay with ERRβ, ERRγ, ERα and Erβ | | | | |
|---|---|---|---|---|
| | IC50 (μM)*** | | | |
| Compound No. | ERRβ* | ERRγ* | ERα* | ERβ* |
| 1-9 | 3.5 | 8.0 | 3.3 | 4.6 |
| 7-2 | 6.7 | 8.0 | 7.8 | 15.0 |
| 7-4 | 7.5 | 8.0 | 5.8 | 16.0 |
| 7-5 | 6.7 | 3.7 | 3.7 | 7.4 |
| 7-7 | 8.0 | 10.0 | 12.5 | 20.0 |
| 7-8 | 3.5 | 6.7 | 2.7 | 6.0 |
| 8-2 | 9.0 | 9.5 | 9.5 | 7.0 |

*HeLa cells were cotransfected with pSG5-ERRb (0.5 mg) or pSG5-ERRg (0.5 mg), and luciferase reporter plasmid containing SF1 binding site and SV40 promoter (0.25 mg). The transfected cells were incubated with chalcones for 24 h. After cells were washed with 1× PBS, luciferase activity was measured.
**HeLa cells were cotransfected with pSG5-ERa (0.01 mg) or pCI-ERb (0.05 mg), and luciferase reporter plasmid containing ERE sequence and SV40 promoter (0.25 mg). The transfected cells were incubated with chalcones in the presence of 100 pM of estradiol for 24 h. After cells were washed with 1× PBS, luciferase activity was measured.
***Values represent the average of at least two experiments.

Example 2

Demonstration of the Suppression Effect of the Chalcones on Interaction Between ERRα and Coactivators (GRIP-1, PGC-1a)

Figure 3:
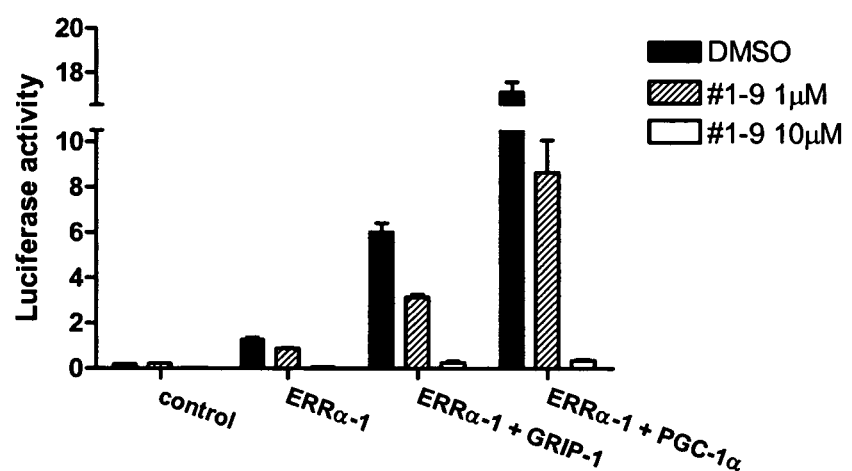
FIG. 3 shows suppression of the coactivation function of GRIP-1 and PGC-1α by Compound No. 1-9 (2',4'-Dihydroxy-2,3-dimethoxychalcone).

To further confirm the antagonism of chalcones, the effect of Compound No. 1-9 on the interaction between ERRα and coactivators (GRIP-1 and PGC-1a) were investigated. HeLa cells were cotransfected with GAL4-binding site containing luciferase reporter and the expression plasmids for ERRα, GRIP-1 and PGC-1a. The ERRα activity was induced 5-fold and 13-fold by cotransfection with GRIP-1 and PGC-1 a, respectively. As shown in FIG. 3, Compound No. 1-9 suppressed the coactivator-induced ERRα activity in a dose-dependent manner. These results support that chalcones are antagonist of ERRα, and may suppress ERRα activity by disrupting the interaction of ERRα with coactivators such as GRIP-1 and PGC-1a.

Referring to FIG. 3, cotransfection experiments with GAL4-binding site containing luciferase reporter (Gal4-TK-Luc; 0.5 μg) and the expression plasmids for ERRα (pM-ERRα LBD; 0.5 μg), GRIP-1 (pSG5-GRIP-1; 0.5 μg) and PGC-1a(pSG5-PGC-1α; 0.25 μg) were performed in HeLa cells. Values represent the mean±SD.

Example 3

Competitive Inhibition of the Binding of [3H] Labeled Genistein by Chalcones

Figure 4:
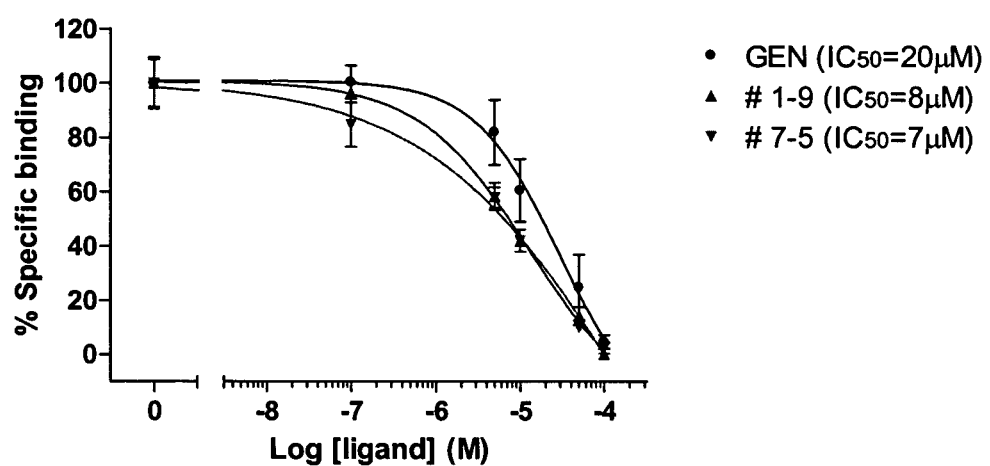
FIG. 4 shows competitive inhibition of the binding of [3H] genistein (GEN) by unlabeled GEN, Compound No. 1-9 (2',4'-Dihydroxy-2,3-dimethoxychalcone), and Compound No. 7-5 (2,2',4'-Trihydroxychalcone).

In addition to reporter activity assay, in order to evaluate the interaction of chalcones with ERRα, a competitive binding assay was performed. SK-BR-3 breast cancer cell line, which is positive for ERRα and negative for ER, was incubated with 1 mM of [3H] labeled genistein, Compound No. 9 (an agonist of ERRα), in the presence of increasing concentrations of the chalcones of Compound Nos. 1-9, 7-2, 7-4, 7-5, 7-7, 7-8, and 8-2. (Compound Nos. 1-9 and 7-5, were the more potent antagonist of ERRα among these seven chalcones). As shown in FIG. 4, Compound Nos. 1-9 and 7-5 competitively inhibited the binding of [3H] labeled genistein in a dose-dependent manner. IC50 of Compound Nos. 1-9 and 7-5 were 8 mM and 7 mM, respectively. These results confirm that chalcones are ligands of ERRα and can compete with genistein for binding to this receptor.

Referring to FIG. 4, SK-BR-3 cells, which are positive for ERRα, were incubated with 1 μM of [3H] GEN and increasing concentrations of unlabeled GEN or Compound Nos. 1-9 or 7-5. After 1 h of incubation, the cells were washed with 1× PBS, and [3H] GEN was then extracted from the cells by an incubation of 30 min in 250 μl of ethanol. Values represent the mean±SD.

Example 4

Figure 5:
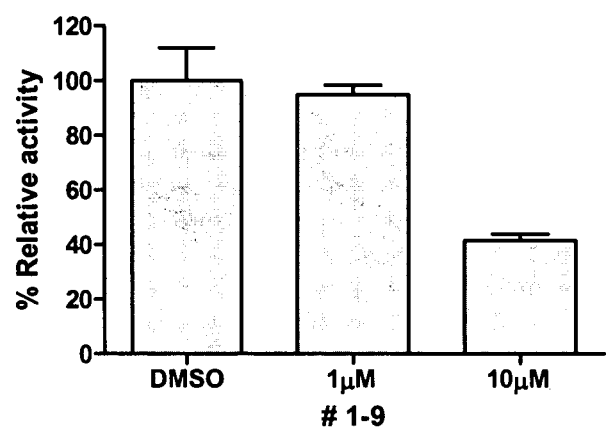
FIG. 5 shows the modulation of ERRα activity by Compound No. 1-9 (2',4'-Dihydroxy-2,3-dimethoxychalcone).

Demonstration of the Interaction of Chalcones with ERRα in Aromatase Expressing Cell Line Aromatase expression is regulated by several promoters, including ERRα modulating promoter I.3. In order to evaluate the effect of chalcones on aromatase activity through ERRα, transient transfection experiments using luciferase reporter plasmid containing a regulatory element S1 and promoter I.3 of human aromatase gene were performed in HepG2 cells. The transfected cells were incubated with chalcones, and luciferase activity was measured. As shown in FIG. 5, through interaction with ERRα, Compound No. 1-9 suppressed the promoter I.3 activity in a dose-dependent manner. These findings suggested that chalcones can affect on aromatase gene expression through ERRα.

Referring to FIG. 5, HepG2 cells were cotransfected with pSG5-ERRα (2 μg) and luciferase reporter plasmid containing S1 and promoter I.3 of human aromatase gene (0.5 μg). The transfected cells were incubated with Compound No. 1-9 for 24 h. After cells were washed with 1× PBS, luciferase activity was measured. Values represent the mean±SD.

Example 5

Suppression of Aromatase Expression by Chalcones

To evaluate the effect of chalcones on aromatase activity, we performed both in vitro assay and in-cell assay with chalcones. As shown in FIG. 6A, increasing concentrations (200 pM-200 mM) of Compound No. 1-9 did not inhibit aromatase activity. In addition, MCF-7 aro cells, which are stable aromatase-expressing breast cancer cell line, were incubated with chalcones. As shown in FIG. 6B, Compound No. 1-9 did not inhibit aromatase activity. The other chalcones also did not affect on aromatase activity in neither in vitro nor in-cell assay (data not shown). On the other hand, in both HepG2 hepatoma cell line and SK-BR-3 breast cancer cell line, Compound No. 1-9 inhibited aromatase activity in a dose-dependent manner, as shown in FIGS. 6C and 6D. These findings suggested that chalcones suppress aromatase expression, and the decrease of aromatase activity in HepG2 and SK-BR-3 cells by chalcones may be result from a reduction of aromatase expression because chalcones did not inhibit aromatase activity neither in vitro nor in MCF-7 aro cells which have artificially expressed aromatase.

Figure 6:
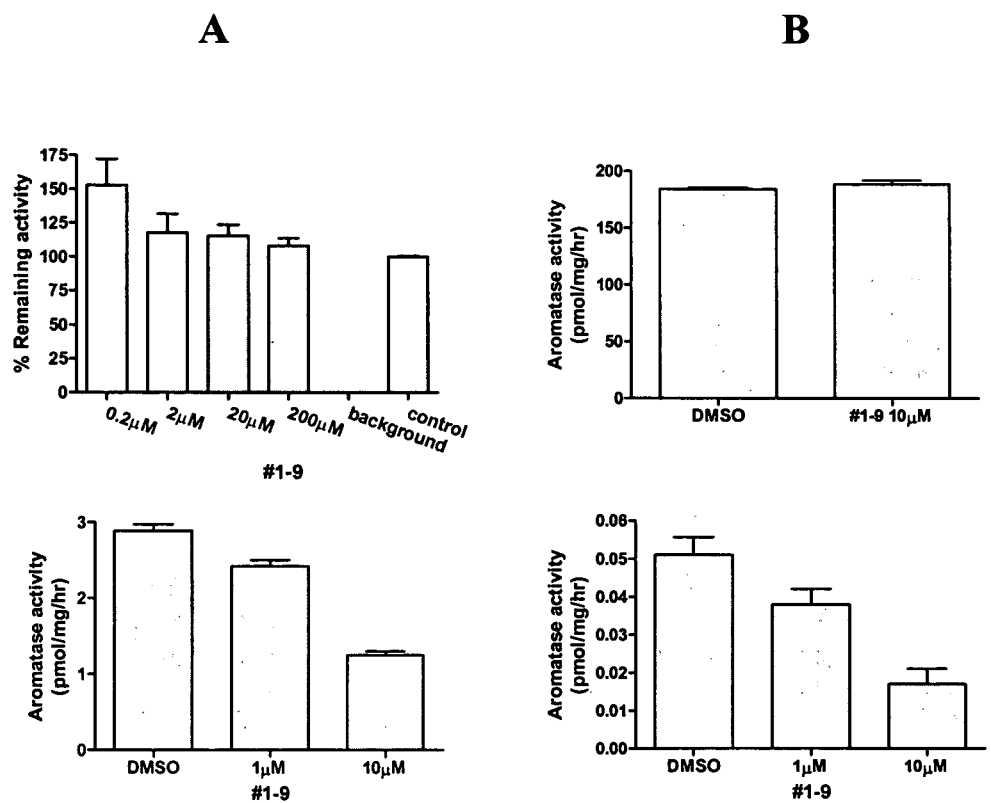
FIG. 6 shows the effect of Compound No. 1-9 (2',4'-Dihydroxy-2,3-dimethoxychalcone) on aromatase activity.

Referring to FIG. 6, the effect of Compound No. 1-9 on aromatase activity was investigated by both in vitro inhibition assay (A) and in-cell aromatase assay (B; MCF-7 aro cells, C; HepG2 cells, D; SK-BR-3 cells). Referring to FIG. 6A, aromatase inhibition study with Compound No. 1-9 was performed on a human placental microsomal aromatase preparation using the assay procedures described in (9). Referring to FIG. 6B, MCF-7 aro cells, which are stable aromatase-expressing cell line generated in our laboratory (10), were incubated with 10 μM of Compound No. 1-9. After 24 h incubation, aromatase activity was measured by [3H] H20 release method. HepG2 cells, as shown in FIG. 6C and SK-BR-3 cells as shown in FIG. 6D were also incubated with Compound No. 1-9 for 24 h, and aromatase activities were measured. Values represent the mean±SD.

Pharmaceutical Indications

Pharmaceutically acceptable carriers for the Compound Nos. 1-9, 7-2, 7-4, 7-5, 7-7, 7-8, 8-2, and 3-15 may include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The formulations useful in the methods of the present invention include one or more ER and/or ERR agonists or antagonists, one or more pharmaceutically acceptable carriers therefor, and optionally other therapeutic ingredients. The formulations may conveniently be presented in unit dosage form and may be prepared by any methods well known in the pharmaceutical arts. The amount of active ingredient, which can be combined with a carrier material to produce a single dosage form, will likely vary depending upon the subject being treated and the particular mode of administration. The amount of ER and/or ERR agonist or antagonist that can be combined with a carrier material to produce a pharmaceutically effective dose will generally be an amount of the ER and/or ERR agonist or antagonist which produces a therapeutic effect. Generally, the amount of the entire volume comprised of the ER and/or ERR agonist or antagonist will range from about one per cent to about ninety-nine percent of the ER and/or ERR agonist or antagonist composition, preferably from about ten per cent to about eighty per cent of the ER and/or ERR agonist or antagonist composition.

Formulations suitable for oral administration may be in the form of capsules, cachets, pills, tablets, lozenges, powders, as granules, bolus, electuary, or a paste, as a solution or a suspension in an aqueous or non-aqueous liquid, as an oil-in-water or water-in-oil liquid emulsion, as an elixir or syrup, or as pastilles (using an inert base, such as gelatin and glycerin, or sucrose and acacia), each containing a predetermined amount of an ER and/or ERR agonist or antagonist as an active ingredient.

In solid dosage forms for oral administration, such as capsules, tablets, pills, powders, granules and the like, the ER and/or ERR agonist or antagonist is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate, solution retarding agents, such as paraffin, absorption accelerators, such as quaternary ammonium compounds; wetting agents, such as, for example, acetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the ER and/or ERR agonist or antagonist therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the ER and/or ERR agonist(s) or antagonist(s) only, or preferentially, in a certain portion of the gastrointestinal tract, optionally, in a delayed manner. Examples of embedding compositions that can be used include polymeric substances and waxes. The ER and/or ERR agonist or antagonist can also be in microencapsulated form, if appropriate, with one or more of the above-described excipients.

Liquid dosage forms for oral administration include pharmaceutically acceptable emulsions, microemulsions, solutions, suspensions, syrups and elixirs. In addition to the ER and/or ERR modulator(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the ER and/or ERR agonist or antagonist, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more ER and/or ERR agonists or antagonists with one or more suitable nonirritating excipients or carriers comprising, for example, cocoa butter, polyethylene glycol, a suppository wax -or a salicylate, and which is solid at room temperature, but liquid at body temperature and, therefore, will melt in the rectum or vaginal cavity and release the active agent.

Formulations for the topical or transdermal administration of an ER and/or ERR agonist or antagonist or an ER and/or ERR agonist or antagonist composition include powders, sprays, ointments, pastes, creams, lotions, gels, solutions, patches and inhalants. The active component may be mixed under sterile conditions with a pharmaceutically acceptable carrier, and with any preservatives, buffers, or propellants that may be required. The ointments, pastes, creams and gels may contain, in addition to the ER and/or ERR agonist or antagonist or the ER and/or ERR agonist or antagonist composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the ER and/or ERR agonist or antagonist or the ER and/or ERR agonist or antagonist composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

ER and/or ERR agonists or antagonists or ER and/or ERR agonist or antagonist compositions can be alternatively administered by aerosol. This is accomplished by preparing an aqueous aerosol, liposomal preparation or solid particles containing the ER and/or ERR agonists or antagonists. A nonaqueous (e. g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver ER and/or ERR agonists or antagonists or ER and/or ERR agonist or antagonist compositions to the body. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Formulations suitable for parenteral administration comprise an ER and/or ERR agonist or antagonist or an ER and/or ERR agonist or antagonist composition in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e. g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, or phenol sorbic acid. It may also be desirable to include isotonic agents, such as sugars, sodium chloride, and the like into the compositions. In addition, prolonged absorption of the injectable pharmaceutical form may be brought about by the inclusion of agents, which delay absorption such as aluminum monostearate and gelatin.

In some cases, in order to prolong the effect of an ER and/or ERR agonist or antagonist, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered formulation is accomplished by dissolving or suspending the ER and/or ERR agonist or antagonist or ER and/or ERR antagonist composition in an oil vehicle.

Injectable depot forms are made by forming microencapsuled matrices of an ER and/or ERR agonist or antagonist or in biodegradable polymers such as polylactide-polyglycolide. Depending on the ratio of the ER and/or ERR agonist or antagonist to polymer, and the nature of the particular polymer employed, the rate of drug release can be controlled. Examples of other biodegradable polymers include poly(orthoesters) and poly(anhydrides). Depot injectable formulations are also prepared by entrapping the ER and/or ERR agonist or antagonist in liposomes or microemulsions that are compatible with body tissue.

The descriptions in the present invention are provided only as examples and should not be understood to be limiting on the claims. Based on the description, a person of ordinary skill in the art may make modifications and changes to the preferred embodiments, which does not depart from the scope of the present invention.

REFERENCES CITED (1) American Cancer Society's Cancer Facts and Figures, www.cancer.org, 2003.
(2) Riggs, L; Hartman, L, Selective Estrogen-Receptor Modulators—Mechanisms of Action and Application to Clinical Practice. New England Journal of Medicine 384:7 2003.
(3) Giguere, V, To ERR in the Estrogen-Pathway. Trends in Endocrinology & Metabolism, Review, Vol. 13, No. 5, 2002.
(4) Coward, P.; Lee, D.; Hull, M. V.; and Lehmann, J. M., 4-Hydroxytamoxifen binds to and deactivates the estrogen-related receptor γ, *PNAS*, 1998, 15, 8880-8884.
(5) Lubczyk, V.; Bachmann, H.; Gust, R., Investigations on estrogen receptor binding. The estrogenic, antiestrogenic, and cytotoxic properties of C2-alkyl-substituted 1,1-bis (4-hydroxyphenyl)-2-phenylethenes, *J. Med. Chem.* 2002, 45, 5358-5364.
(6) Lubczyk, V.; Bachmann, H.; Gust, R., Antiestrogenically active 1,1,2-tris(4-hydroxyphenyl)alkenes without basic side chain: synthesis and biological activity, *J. Med. Chem,* 2003.
(7) Finkel T; JBC; 22384348; Schreiber S N; Kralli T; JBC, 278(11), 9013-9018, Mar. 14, 2003.
(8) Katzenellenbogen, B. S.; Norman, M. J.; Eckert, R. L.; Peltz, S. W.; Mangel, W. F., Bioactivities, estrogen-receptor interactions, and plasminogen activator-inducing activities of tamoxifen and hydroxytamoxifen isomers in MCF-7 human-breast cancer-cells *Cancer Res.* 1984, 44, 112-119.
(9) Schnrider, M. R.; von Angerer, E.; Schonenberger, H.; Michel, R. T.; Fortmeyer, H. P., 1,1,2-Triphenylbut-1-enes: relationship between structure, estradiol receptor affinity, and mammary tumor inhibiting properties *J. Med. Chem.* 1982, 25, 1070-1077.
(10) Tremblay G B, Bergeron D, Giguere V., Endocrinology; 142(10):4572-5, October 2001.
(11) Dodds, E. C.; Golberg, L.; Lawson, W.; Robinson, R. Synthetic estrogenic compounds related to stilbene and diphenylethane I. *Proc. R. Soc.* London Ser. B 1989, 127, 140-167.

(12) McMurry, J. E.; Fleming, M. P., Improved procedures for the reductive coupling of carbonyls to olefins and for the reduction of diol to olefins, *J. Org. Chem.* 1976, 41, 896.

(13) Gauthier, S.; Mailhot, J.; Labrie, F., New highly stereoselctive synthesis of (Z)-4-hydroxytamoxifen and (Z)-4-hydroxytoremifene via McMurry reaction, *J. Org. Chem,* 1996, 61,3890-3893.

(14) Detsi, A.; Koufaki, M.; Calogeropoulou, T., Synthesis of (Z)-4-hydroxytamoxifen and (Z)-2-[4-[1-(p-hydroxyphenyl)-2-phenyl]-1-butenyl] phenoxyacetic acid, *J. Org. Chem.,* 2002, 67, 4608-4611.

(15) Ichida, M.; Nemoto, S; Finkel, T., Identification of a specific molecular repressor of the peroxisome proliferator-activated receptor gamma Coactivator-1 alpha., *J. Biol Chem,* 2002, 52: 50991-95.

(16) Liu, D.; Zhang, Z.; Gladwell, W.; and Teng, C, Estrogen Stimulates Estrogen-Related Receptor a Gene Expression Through Conserved Hormone Response Elements, Endocrinology, July 2003, 10.1210/en.2003-0432.

(17) Robertson, D. W.; Katzenellenbogen, J. A.; Long, D. J.; Rorke, E. A.; Katzenellenbogen, B. S. J. Steroid Biochem. 1982, 16, 1.

(18) Jordan, V. C., Antiestrogens and selective estrogen receptor modulators as multifunctional medicines. 1. Receptor interactions, *J. Med. Chem.,* 2003, 46, 883-908.

(19) Jarman, M.; McCague, R. *J. Chem. Research* (S), 1985, 116.

(20) Magdani, L.; Hutak, A.; Szatmari, E.; Simoni, I.; Halmos, J.; Nemere, F. *Belg. P.,* 1982, 892 662.

(21) Yang, C., Zhou, D., and Chen, S., Modulation of aromatase expression in the breast tissue by ERRα-1 orphan receptor. Cancer Res., 58:5695-5700, 1998.

(22) Ariazi, E. A., Clark, G. M. and Mertz, J. E. Estrogen-related receptor a and estrogen-related receptor g associate with unfavorable and favorable biomarkers, respectively, in human breast cancer. Cancer Res., 62: 6510-6518, 2002.

(23) Luo, J., Sladek, R., Carrier, J., Bader, J. A., Richard, D. and Giguere, V. Reduced fat mass in mice lacking orphan nuclear receptor estrogen-related receptor alpha. Mol. Cell. Bio., 23: 7947-7956, 2003.

(24) Sumi, D. and Ignarro, L. J. Estrogen-related receptor alpha up-regulates endothelial nitric oxide synthase expression. Proc. Natl. Acad. Sci. USA, in press, 2003.

(25) Schreiber, S. N., Emter, R., Hock, M. B., Knutti, D., Cardenas, J., Podvinec, M., Oakeley, E. J. and Kralli, A. The estrogen-related receptor a (ERRa) functions in PPARg coactivator 1a (PGC-1a)-induced mitochondrial biogenesis. Proc. Natl. Acad. Sci., 101: 6472-6477, 2004.

(26) Mootha, V. K., Handschin, C., Arlow, D., Xie, X., St. Pierre, J., Sihag, S., Yang, W., Altshuler, D., Puigserver, P., Willy, P. J., Schulman, I. G., Heyman, R. A., Lander, E. S. and Spiegelman, B. M. ERRα and Gabpa/b specify PGC-1a-dependent oxidative phosphorylation gene expression that is altered in diabetic muscle. Proc. Natl. Acad. Sci., 101: 6570-6575, 2004.

(27) Willy, P. J., Murray, I. R., Qian, J., Busch, B. B., Stevens, Jr., W. C., Martin, R., Mohan, R., Zhou, S., Ordentlich, P., Wei, P., Sapp, D. W., Horlick, R. A., Heyman, R. A. and Schulman, I. G. Regulation of PPARr coactivator 1a (PGC-1a) signaling by an estrogen-related receptor a (ERRa) ligand. Proc. Natl. Acad. Sci., 101: 8912-8917, 2004.

(28) Suetsugi, M., Su, L., Karlsberg, K., Yuan, Y.-C. and Chen, S. Flavone and isoflavone phytoestrogens are agonists of estrogen-related receptors. Molecular Cancer Res., 1: 981-991, 2003.

(29) Zhou, D., Quoch, K. M., Yang, C., Pohajdak, B., and Chen, S. PNRC: a proline-rich nuclear receptor coregulatory protein that modulates transcriptional activation of multiple nuclear receptors including orphan receptors SF1 and ERRα1. Molecular Endocrinol., 14: 986-996, 2000.

Other References

Karnik, P. S.; Kulkarni, S.; Liu, X. P.; Budd, G. T.; Bukowski, R. M. Estrogen receptor mutations in tamoxifen-resistant breast cancer. Cancer Res. 1994, 54, 349-353.

Giguere, V.; Yang, N.; Segui, P.; Evans, R. M., Identification of a new class of steroid hormone receptors. *Nature* 1988, 331, 91-94.

Schneider, M. R., 2-Alkyl-substutited 1,1-bis (4-acetoxyphenyl)-2-phenylethenes. Estrogen receptor affinity, estrogenic and antiestrogenic properties, and mammary tumor inhibiting properties. *J. Med. Chem.* 1986, 29, 1494-1498.

What is claimed is:

1. A composition for treating an estrogen receptor mediated disorder, comprising a therapeutically effective amount of a compound selected from the group consisting of Compound Nos. 1-9, 7-2, 7-4, 7-5, 7-7, 7-8, and 8-2 or a pharmaceutically acceptable salt thereof for treating an estrogen receptor mediated disorder;

a pharmaceutically acceptable carrier, wherein the pharmaceutically acceptable carrier is selected from the group consisting of sugar, sugar alcohol, starch, cellulose or cellulose derivatives, tragacanth, malt, gelatin, talc, wax, oil, glycol, glycerol, ester, ethyl oleate, ethyl laurate, agar, magnesium hydroxide, aluminum hydroxide, alginic acid, isotonic saline, Ringer's solution, sodium citrate, dicalcium phosphate, silicic acid, carboxymethylcellulose, alginates, polyvinyl pyrrolidone, disintegrating agents, calcium carbonate, alginic acid, silicates, solution retarding agents, paraffin, absorption accelerators, quaternary ammonium compound, wetting agents, acetyl alcohol, glycerol monostearate, kaolin, bentonite clay, lubricant, talc, calcium stearate, magnesium stearate, and sodium lauryl sulfate; and optionally, another therapeutic ingredient.

2. The composition of claim 1 wherein the compound modulates an estrogen receptor.

3. The composition of claim 1 wherein the compound antagonizes an estrogen receptor.

4. The composition of claim 3 wherein antagonizing an estrogen receptor comprises reducing the activation of the estrogen receptor.

5. The composition of claim 3 wherein antagonizing an estrogen receptor comprises preventing the activation of the estrogen receptor.

6. A composition for treating an estrogen related receptor mediated disorder, comprising a therapeutically effective amount of a compound selected from the group consisting of Compound Nos. 1-9, 7-2, 7-4, 7-5, 7-7, 7-8, and 8-2 or a pharmaceutically acceptable salt thereof for treating an estrogen related receptor mediated disorder;

a pharmaceutically acceptable carrier, wherein the pharmaceutically acceptable carrier is selected from the group consisting of sugar, sugar alcohol, starch, cellulose or cellulose derivatives, tragacanth, malt, gelatin, talc, wax, oil, glycol, glycerol, ester, ethyl oleate, ethyl laurate, agar, magnesium hydroxide, aluminum hydroxide, alginic acid, isotonic saline, Ringer's solution, sodium citrate, dicalcium phosphate, silicic acid, carboxymethylcellulose, alginates, polyvinyl pyrrolidone, disintegrating agents, calcium carbonate, alginic acid, silicates, solution retarding agents, paraffin, absorption accelerators, quaternary ammonium compound, wetting agents, acetyl alcohol, glycerol monostearate, kaolin, bentonite clay, lubricant, talc, calcium stearate, magnesium stearate, and sodium lauryl sulfate; and optionally, another therapeutic ingredient.

7. The composition of claim 6 wherein the compound modulates an estrogen related receptor.

8. The composition of claim 6 wherein the compound antagonizes an estrogen related receptor.

9. The composition of claim 8 wherein antagonizing an estrogen related receptor comprises reducing the activation of the estrogen related receptor.

10. The composition of claim 8 wherein antagonizing an estrogen related receptor comprises preventing the activation of the estrogen related receptor.

11. The composition of claim 1 wherein the therapeutically effective amount of a compound is selected from the group consisting of a dosage between 1 mg/day and 1 g/day, between 20 mg/kg and 750 mg/kg per day, or between 50 mg/day and 500 mg/day.

12. The composition of claim 1 wherein the therapeutically effective amount of a compound is a dosage between 1 mg/day and 1 g/day.

13. The composition of claim 1 wherein the therapeutically effective amount of a compound is a dosage between 20 mg/kg and 750 mg/kg per day.

14. The composition of claim 1 wherein the therapeutically effective amount of a compound is a dosage between 50 mg/day and 500 mg/day.

15. The composition of claim 6 wherein the therapeutically effective amount of a compound is selected from the group consisting of a dosage between 1 mg/day and 1 g/day, between 20 mg/kg and 750 mg/kg per day, or between 50 mg/day and 500 mg/day.

16. The composition of claim 6 wherein the therapeutically effective amount of a compound is a dosage between 1 mg/day and 1 g/day.

17. The composition of claim 6 wherein the therapeutically effective amount of a compound is a dosage between 20 mg/kg and 750 mg/kg per day.

18. The composition of claim 6 wherein the therapeutically effective amount of a compound is a dosage between 50 mg/day and 500 mg/day.

19. A composition for treating an estrogen receptor mediated disorder, comprising a therapeutically effective amount of Compound No. 1-9 or a pharmaceutically acceptable salt thereof for treating an estrogen receptor mediated disorder; a pharmaceutically acceptable carrier and another therapeutic agent.

20. The composition of claim 19 wherein the pharmaceutically acceptable carrier is selected from the group consisting of sugar, sugar alcohol, starch, cellulose or cellulose derivatives, tragacanth, malt, gelatin, talc, wax, oil, glycol, glycerol, ester, ethyl oleate, ethyl laurate, agar, magnesium hydroxide, aluminum hydroxide, alginic acid, isotonic saline, Ringer's solution, sodium citrate, dicalcium phosphate, silicic acid, carboxymethylcellulose, alginates, polyvinyl pyrrolidone, disintegrating agents, calcium carbonate, alginic acid, silicates, solution retarding agents, paraffin, absorption accelerators, quaternary ammonium compound, wetting agents, acetyl alcohol, glycerol monostearate, kaolin, bentonite clay, lubricant, talc, calcium stearate, magnesium stearate, and sodium lauryl sulfate.

21. The composition of claim 19 wherein the therapeutic agent selected is a radiotherapeutic agent or a chemotherapeutic agent, or a combination thereof.

22. The composition of claim 19 wherein the therapeutic agent selected is a radiotherapeutic agent.

23. The composition of claim 19 wherein the therapeutic agent selected is a chemotherapeutic agent.

24. The composition of claim 19 wherein the therapeutically effective amount of a compound is selected from the group consisting of a dosage between 1 mg/day and 1 g/day, between 20 mg/kg and 750 mg/kg per day, or between 50 mg/day and 500 mg/day.

25. The composition of claim 19 wherein the therapeutically effective amount of a compound is a dosage between 1 mg/day and 1 g/day.

26. The composition of claim 19 wherein the therapeutically effective amount of a compound is a dosage between 20 mg/kg and 750 mg/kg per day.

27. The composition of claim 19 wherein the therapeutically effective amount of a compound is a dosage between 50 mg/day and 500 mg/day.

\* \* \* \* \*

UNITED STATES PATENT AND TRADEMARK OFFICE
CERTIFICATE OF CORRECTION

PATENT NO. : 9,763,961 B2
APPLICATION NO. : 11/400024
DATED : September 19, 2017
INVENTOR(S) : Shiuan Chen Page 1 of 1

It is certified that error appears in the above-identified patent and that said Letters Patent is hereby corrected as shown below:

In the Specification

Statement of Government Interest section, Column 1, Lines, 16-18, please delete:
"This invention was supported in part by NIH Grant No. ES08258. The United States govermnent may have certain rights in this invention."

And insert:
--This invention was made with government support under ES008258 awarded by the National Institutes of Health. The government has certain rights in the invention.--

Signed and Sealed this
Eighth Day of April, 2025

Coke Morgan Stewart
*Acting Director of the United States Patent and Trademark Office*